United States Patent [19]
Hochstetler et al.

[11] 3,962,148
[45] June 8, 1976

[54] ODORANT COMPOSITIONS CONTAINING 4,4,6-TRIMETHYL-2-CYCLOHEXENONE

[75] Inventors: Alan R. Hochstetler, Franklin Lakes; Frederick Louis Schmitt, Holmdell, both of N.J.

[73] Assignee: Givaudan Corporation, Clifton, N.J.

[22] Filed: July 3, 1975

[21] Appl. No.: 592,963

[52] U.S. Cl. .......................... 252/522; 260/586 C; 260/586 R
[51] Int. Cl.$^2$ ......................................... C11B 9/00
[58] Field of Search .................................. 252/522

[56] References Cited
UNITED STATES PATENTS 2,845,460   7/1958   Isler et al. .......................... 252/522
3,124,614   3/1964   Daukert et al. ..................... 252/522

OTHER PUBLICATIONS

Steffen Arctauder, Perfume and Flavor Chemicals, vol. I, Published by the Author, 1969, Montclair, N.J., Monograph 967.
J. Org. Chem. 29, 2501, 1964.
J. Org. Chem. 33, 4060, 1968.
Org. Reactions 16, 1, 1968.

*Primary Examiner*—Veronica O'Keefe
*Attorney, Agent, or Firm*—Thomas Cifelli, Jr.

[57] ABSTRACT

Method for preparing 4,4,6-trimethyl-2-cyclohexenone, its use in odorant compositions and a novel intermediate thereof.

8 Claims, No Drawings

ODORANT COMPOSITIONS CONTAINING 4,4,6-TRIMETHYL-2-CYCLOHEXENONE

BACKGROUND OF THE INVENTION

1. Field of the Invention
Odorant Compositions.
2. Description of the Prior Art

Many of the important fragrance notes used in the art of perfumery are provided by natural materials. The supply of these natural oils is often subject to the vagaries common to agricultural products such as poor crop years, political turmoil, hoarding, etc. Quite often these uncontrolled variables cause industrial consumers to deal with fluctuating prices and inadequate supplies to fill needs.

There is accordingly a continuing effort to provide economical synthetic products which can be used, either alone or in combination with other materials, to provide compositions which can be used as substitutes or as partial substitues for these natural oils.

While the 4,4,6-trimethyl-2-cyclohexenone utilized in this invention has been reported (J. Org. Chem., 33, 4060 (1968)) there was no mention of the odor of this compound. Its utility as an odorant and especially as a valuable component in the preparation of substitutes for certain natural oils has heretofore not been known.

SUMMARY OF THE INVENTION

The 4,4,6-trimethyl-2-cyclohexenone of this invention has a warm, herbaceous, minty, camphoraceous odor. It is particularly useful in providing nuances to ordorant compositions. It can be used as a valuable ingredient in perfume compositions. It can also be used in combination with other materials in providing a synthetic substitute for certain natural oils. For example, it can be used as the major ingredient in a synthetic cedar leaf oil.

There is also provided herein an improved process for preparing the 4,4,6-trimethyl-2-cyclohexenone.

The 4,4,6-trimethyl-2-cyclohexenone used in this invention can be prepared by reacting isobutyraldehyde with methyl isopropenyl ketone [J. Org. Chem. 33, 4060 (1968)]. Typically, the reactants can be reacted in an aqueous solution using a hydroxide base as catalyst. Normally the reaction is carried out using equimolar amounts of reactants, a portion of methanol to render the reaction solution more homogeneous and a base catalyst such as sodium or potassium hydroxide. Once admixed, it is preferred to heat the reaction mixture to 60°-80°C for a period of about 1 hour. Normal variations in procedure such as increasing the amount of a particular reactant, changing the order and manner by which each reactant is added, temperature changes etc. do not seem to have any significant effect on the yield. Following the procedure as described, a yield of about 43% of theory is obtained which is comparable with that reported (J. Org. Chem., 33, 4060 (1968)).

It has now been found that a significant improvement can be made in the process by adding an additional acid catalyzed dehydration step. This improved process provides a 59% yield as opposed to the 43% obtained without this improvement. (In essence the improved process provides 37% more material than does the original process.)

It has now been found that the lower yields of the unimproved process are due to the surprising stability of an intermediate product, the novel 5-hydroxy-2,4,4-trimethylcyclohexanone. While it is known that, under basic conditions, ketols (J. Org. Chem., 29, 2501 (1964)) and/or aldols (Organic Reactions, 16, 1, (1968)) of this type can be isolated at low temperatures, such compounds dehydrate readily under the higher temperatures employed in the present process. Under the normal conditions the reaction is assumed to proceed as follows:

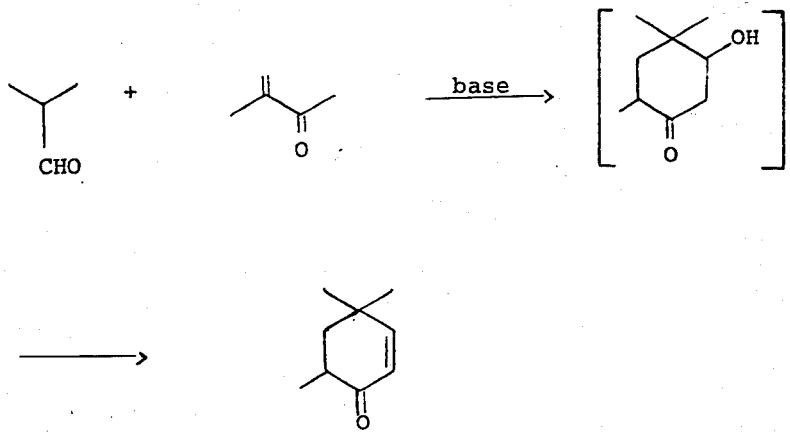

While it is not now known whether there are two pathways (one producing ketol and another producing the cyclohexenone), whether there are two ketol isomers (one which dehydrates and the other which does not); whether there is another common intermediate which produces both ketol and cyclohexenone or whether there is some other mechanism, it is herein shown that a ketol which does not readily dehydrate under the basic reaction conditions can be isolated and can then be quantitatively dehydrated to the desired 4,4,6-trimethyl-2-cyclohexenone.

While the novel 5-hydroxy-2,4,4-trimethylcyclohexanone can be isolated as shown in the examples, it is preferred to take up the crude organic reaction product in a solvent, preferably a known water azeotroping solvent such as benzene, cyclohexane etc. whereby the acid-catalyzed dehydration step can be carried out with concomitant azeotropic removal of the water generated.

The dehydration is effected with a catalytic amount, preferably about 0.1 to 2.5% by weight of an acid catalyst such as an organic or inorganic acid catalyst, for example, an inorganic catalyst such as phosphoric acid, a lower alkyl phenyl sulfonic acid such as para-toluenesulfonic acid or a polycarboxylic acid such as citric acid, oxalic acid or tartaric acid. Preferably the reaction is conducted at the boiling point of the two phase azeotrope that is formed until no further water of dehydration is formed. Any method known in the art for dehydrating alcohols which is not unduly severe so as to significantly destroy the desired product would be applicable. Acidic dehydration procedures are commonly known in the art and the amounts of acid of particular strengths used is easily determined from the known art.

Alternatively, the 4,4,6-trimethyl-2-cyclohexenone can be prepared by reacting 3-hydroxymethyl-2-butanone with isobutyraldehyde. The 3-hydroxymethyl-2-butanone is prepared by reacting 2-butanone with formaldehyde. While it has not been shown, it is assumed that the hydroxymethyl-2-butanone dehydrates under the reaction conditions to provide methyl isopropenyl ketone which then reacts as previously described. Although this procedure results in lower overall yields than when methyl isopropenyl ketone is used, it provides a process which utilized the readily available 2-butanone and formaldehyde rather than methyl isopropenyl ketone which is not readily available in commercial quantities. The procedure also avoids the need for special precautions for storing or handling the methyl isopropenyl ketone (a known lachrymator).

The 4,4,6-trimethyl-2-cyclohexenone has the warm herbaceous, minty, camphoraceous notes normally found in certain natural oils such as cedar leaf oil. It has been known that the major constituent of cedar leaf oil is the (—)-thujone, a bicyclic terpene having a cyclopropyl ring, and it is this constituent of the cedar leaf oil which is considered to have the odor characteristics most like the 4,4,6-trimethyl-2-cyclohexenone. It is also known that (—)-thujone is the major constituent of a number of natural oils and may be present in other oils as yet unanalysed. Included among the oils in which it is known that thujone is the predominant constituent are the oil of Thuja occidentalis L., also known as cedar leaf oil (Can. J. Chem., 39, 1200 (1961); the oil of Thuja plicata D., another cedar leaf oil (Phytochemistry, 1, 195 (1962)); Dalmatian sage oil from Salvina officinalias L. (Parf. Cosm. Sav. France, 1, 256 (1971)); wormwood oil from Artemisia absinthium L.; and Tansey oil from Tanacetum vulgare L. A host of other oils of perhaps less commercial value than the above can be found by consulting Gildmeister and Hoffman, "Die Atherischen Ole" Vol IIIc pp. 271–3, Akademie-Verlag, Berlin (1963).

The known chemical and physiological properties of thujone accent further the desirability of providing synthetic substances for those thujone-containing natural oils presently used. Stephan Arctander in his "Perfume and Flavor Chemicals", Volume II, Montclair, N.J., (1969) states, in reference to thujone, that "The material tends to darken and resinify upon exposure to air" and also that "Thujone is by some authorities considered one of the most toxic of all commonly occurring components of essential oils". It is therefore of great value to provide compositions which are more stable and less toxic than those which contain thujone.

Heretofore, attempts to provide synthetic replacements for the aforementioned natural oils have been hampered by the lack of a readily available substance which would provide the warmherbaceous, minty-camphoraceous odor attributed to the (—)-thujone content of these oils. An economically feasible commercial synthesis of (—)-thujone (see structure I below) is not available.

The 4,4,6-trimethyl-2-cyclohexenone, having a structure, II, totally unrelated to the naturally occurring thujone, I, provides

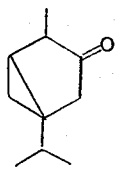

I

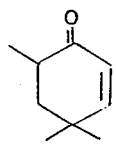

II

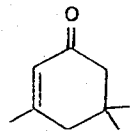

III

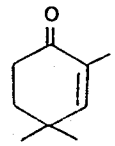

IV the nuances necessary to enable its use as the major constituent in synthetic substitutes for many natural oils which contain thujone.

Compounds isomeric to the 4,4,6-trimethyl-2-cyclohexenone of this invention have not found wide use in the perfumery arts. Although listed in Stephan Arctander's "Perfume and Flavor Chemicals", Volume II, Montclair, N.J., (1969); isophorone (structure III above) has not found significant use in the perfume arts. While Arctander describes the odor as pungent, sweet camphoraceous, he also reveals that it is only "occasionally used in perfumery" and that often times a customer who used it as a solvent requests "a perfume with which he can mask the odor of iso-Phorone".

The 2,2,4-trimethyl-2-cyclohexenone (structure IV above) is described as "powerful and rather pungent, but in dilution pleasant, warm-herbaceous and minty camphoraceous . . . reminiscent of Tansey oil or Dalmation Sage Oil". While Arctander reveals that "this ketone has been suggested for use in perfume compositions", [the compound and its odor description (tansey-like) has been known since 1902 (Wallach, Annalen 324, 97 (1902)], the 2,4,4-trimethyl-2-cyclohexenone has not as yet found significant use in perfumery.

A direct comparison of the three isomeric ketones reveals that their odors are quite different. The isophorone III was considered by the perfumers as pungent, unpleasant and totally devoid of any warm herbaceous notes. The 2,2,4-trimethyl-2-cyclohexenone IV though far superior to the isophorone, was still somewhat pungent and had notes that made it undesirable in a synthetic natural oil such as cedar leaf oil. The compound used in this invention (II) showed much more of the characteristic green-herbaceousness characteristic of the contribution to such oils made by the naturally occurring thujone.

When a six membered panel was asked to compare natural thujone to coded samples, one of which contained compound II and the other of which contained compound IV, all six independently matched compound II as being closer to the natural thujone.

When used in a synthetic cedar leaf oil (see Example I), compound II provides the warm, green, herbaceous notes normally associated with thujone in the natural oil. When compound IV is used, the composition is "flat" and lacks "lift" and "roundness". The composition emits musty, minty, cineol-like and piney notes and lacks the desired green herbaceous character of natural cedar leaf. Whereas the 4,4,6-trimethyl-2-cyclohexenone (compound II) of this invention finds utility in the preparation of a fine synthetic cedar leaf oil, the 2,2,4-trimethyl-2-cyclohexenone (compound IV) does not.

In general perfumery, the 4,4,6-trimethyl-2-cyclohexenone is preferred because it lacks the pungent note of compound IV and can be used in greater dilution because of an unexpectedly high threshold level as compared to IV. Most importantly, even though the verbal description of the two odors may rely on some of the same words, the odors are quite different and one is not a substitute for the other. Despite our semantic difficulties, compound II now finds important use in perfumery while compound IV does not, even though the latter has been known (with odor description) since 1902.

The threshold level of the two compounds were compared by the test as described in Example VII. By this test, which was completely blind, it was found that the threshold level differences of the compound II used in this invention and the compound IV was on the order of 10 times. That is, the compound II could be detected in solutions which were ten times more dilute than those at which the comparison compound IV could not be detected. In practical terms this means that we can get the same odor impact with 1/10 as much II as IV. (It is, of course, understood that the odor quality is not the same since the compounds smell differently).

In addition to its great utility in the preparation of certain natural oils, the 4,4,6-trimethyl-2-cyclohexenone of this invention is generally useful in a variety of perfume compositions.

It has been found that the addition of low concentrations, i.e. about 1% of the total perfume base, gives lift and freshness to the top note of floral fragrances such as lilac, hyacinth and gardenia. It also appears to intensify and enhance the middle notes of such fragrances.

The addition of this compound to a fougere type fragrance at low concentrations seems to intensify the lavender notes. In other applications it intensifies animal notes. It also adds to the freshness of a cologne.

At higher concentrations the effect of the chemical is more pronounced and in florals it can change a distinctly green character into a distinctly herbaceous character.

Surprisingly, this compound of simple structure makes a valuable contribution to a variety of fragrances. It is useful not only for its own odor, but as a valuable additive to modify and complement the odors of other fragrance materials.

The following examples are intended to illustrate embodiments of this invention as it is now preferred to practice it. It will be understood that such examples are merely illustrative and the invention is to be limited thereto only as indicated in the claims. Unless otherwise indicated, perfume ingredients are given in parts/t-housand by weight, weights are in grams, infrared values are in $cm^{-1}$, nmr spectra were run in $CDCl_3$ and chemical shift values are given in $\delta$ values with respect to TMS.

EXAMPLE I

A synthetic cedar leaf oil replacement was formulated employing 4,4,6-trimethyl-2-cyclohexenone as an ingredient. The formula is as follows:

| Cedar Leaf Oil Type | |
|---|---|
| Camphene | 20 |
| β-Pinene | 35 |
| Myrcene | 13 |
| d-Limonene | 36 |
| Fenchone | 78 |
| Camphor | 25 |
| Terpinen-4-ol | 27 |
| Bornyl acetate | 59 |
| Diethyl phthalate | 120 |
| 4,4,6-Trimethyl-2-cyclohexenone | 587 |
| | 1000 |

The addition of 4,4,6-trimethyl-2-cyclohexenone produces the desired evergreen, herbaceous, camphoraceous top and middle notes which are characteristic of the cedar leaf odor. The 4,4,6-trimethyl-2-cyclohexenone makes an odor contribution to the above cedar leaf oil type comparable to that of (−)-thujone in natural cedar leaf oil.

When the isomeric 2,4,4-trimethyl-2-cyclohexenone is substituted for the 4,4,6-trimethyl-2-cyclohexenone the composition is "flat" and lacks the "lift" and "roundness" of the original. The composition lacks the green herbaceousness of the natural cedar leaf and is also characterized by undesirable musty, minty cineol-like and piney notes.

EXAMPLE II

A synthetic tansey oil replacement was formulated employing 4,4,6-trimethyl-2-cyclohexenone (Tansey 1) as an ingredient and is compared with one using thujone (Tansey 2). The formula is as follows:

| TANSEY OIL TYPE | Tansey 1 | Tansey 2 |
|---|---|---|
| α-Pinene | 2 | 2 |
| β-Pinene | 1 | 1 |
| Camphene | 2 | 2 |
| Limonene | 1 | 1 |
| 1,8-Cineole | 23 | 23 |
| p-Cymene | 4 | 4 |
| Terpinolene | 1 | 1 |
| Camphor | 8 | 8 |
| Terpinen-4-ol | 10 | 10 |
| 1-Carvotanacetone | 7 | 7 |
| 1-Borneol | 8 | 8 |
| 1-Carvone | 58 | 58 |
| Bisabolene | 37 | 37 |
| Thujone | — | 120 |
| 4,4,6-Trimethyl-2-cyclohexenone | 58 | — |
| Diethyl phthalate | 780 | 718 |
| | 1000 | 1000 |

In this example the odor of the base lacking the 4,4,6-trimethyl-2-cyclohexenone is not very reminiscent of tansey oil. The addition of only 6% by weight of 4,4,6-trimethyl-2-cyclohexenone brings the odor quite close to the spicy herbaceous character of tansey oil. In order to achieve the same effect in this base, thujone (Tansey 2) must be used at a 12% weight level.

EXAMPLE III

To a mixture of isobutyraldehyde (382 g, 5.3 mole) in 400 ml of 0.8 M aqueous sodium hydroxide was added methyl isopropenyl ketone (420 g, 5.0 mole) over a 1 hr period at 25°. The mixture was then heated to 75° for 1 hr. The mixture was cooled, and the layers were separated. The organic phase was washed neutral with water. Distillation of this organic material afforded 297 g (2.15 mole, 43% yield) of the desired 4,4,6-trimethyl-2-cyclohexenone, bp 68°–69° at 10mm, $n_D^{20}$ 1.4685, with an infrared and nmr spectra identical with that reported in the literature (JOC 33, 4060 (1968)). Continued distillation afforded a new material (116 g) with a boiling point of 100° to 120° at 0.5mm. This material slowly crystallized and was filtered and washed with hexane. These crystals proved to be 5-hydroxy-2,4,4-trimethylcyclohexanone and exhibited the following spectral characteristics: mp 105°–106°; ir (KBr) 3360 (OH), 1685 (C=O), 1250, 1195, 1135, 1111, 1029, 983 cm$^{-1}$; nmr (CDCl$_3$) 0.98 (d, J=6.5Hz, 3H), 1.04 (s, 3H), 1.22 (s, 3H), 1.53 (d,d,d, J=13, 8, 1.5 Hz, 1H), 1.90 (d, J=13 Hz, 1H), 2.35 (d,d, J=15, 3 Hz, 1H), 2.62 (d,d, J=15, 3 Hz, 1H), 3.85 (m, 1H); mass spectrum (m/e, (relative intensity) 156 (8), 138 (2), 100 (100), 72 (35), 70 (33) 68 (37), 56 (80), 43 (38), 41 (37).

Treatment of the above 5-hydroxy-2,4,4-trimethylcyclohexanone with a catalytic amount (.05% by weight of ketol charged) of p-toluenesulfonic acid with azeotropic removal of water afforded a quantitative yield of the desired 4,4,6-trimethyl-2-cyclohexenone (II).

EXAMPLE IV

The procedure of example III was employed on 12 moles of isobutyraldehyde, 11 moles of methyl isopropenyl ketone and 800 ml of 0.8 M aqueous sodium hydroxide solution. After the reaction was completed the aqueous layer was removed. To the residual organic phase was added an equal volume of benzene and a catalytic amount (ca. 5 g) of p-toluenesulfonic acid. The reaction mixture was heated at reflux with concomitant removal of water via a Dean Stark trap. The usual workup and distillation afforded 897 g (59%) of the desired 4,4,6-trimethyl-2-cyclohexenone (II) with physical constants and spectral data identical with that isolated in Example III. Continued distillation afforded no material containing the 5-hydroxy-2,4,4-trimethylcyclohexanone isolated in Example III where the acid treatment step was omitted.

EXAMPLE V

A. 3-Hydroxymethyl-2-butanone

To paraformaldehyde (270 g, 9 mol) and 2-butanone (3000 g, 41.6 mol) in a reaction flask is added a solution of 1.5 g sodium hydroxide in 25 ml of methanol. The reaction mixture is maintained at 45°C for 2 hours. Acetic acid (1.0 g) is added and the excess 2-butanone is removed by distillation. Further distillation at reduced pressure yields 502 g (4.9 mol) 3-hydroxymethyl-2-butanone (bp 78°–80° at 20mm, $n_D^{20}$ 1.4325).

B. 4,4,6-Trimethyl-2-cyclohexenone

The procedure of Example IV is repeated using 502 g (4.9 mol) of 3-hydroxymethyl-2-butanone in place of methyl isopropenyl ketone, 352 g (4.9) moles of isobutyraldehyde and 200 g of a 5% sodium hydroxide solution.

This procedure yielded 308.0 g (45.5% theory) of 4,4,6-trimethyl-2-cyclohexenone identical to that isolated in Example III.

EXAMPLE VI

The following example illustrates the use of 4,4,6-trimethyl-2-cyclohexenone to suppress the green notes in a floral composition and provide a herbaceous character to that composition.

In this example, 5% of the 4,4,6-trimethyl-2-cyclohexenone was added to the hyacinth-type composition shown below. This addition changed the very intense pungent green-floral odor of hyacinth to a rounded, herbaceous odor. Various degrees of herbaceousness can be achieved depending on the level of Compound A added.

| Hyacinth-type Composition | Parts/thousand |
| --- | --- |
| Phenyl ethyl alcohol | 150 |
| Hydroxycitronellal | 59 |
| Benzyl acetate | 15 |
| Phenyl ethyl formate | 4 |
| Indole, 10% Diethyl phthalate | 36 |
| Hyacinth body | 16 |
| Hydratropic alcohol | 25 |
| Phenyl acetaldehyde dimethyl acetal | 16 |
| Hydratropic aldehyde dimethyl acetal | 25 |
| Phenyl acetaldehyde, pure 10% | 12 |
| Galbanum oil | 8 |
| Musk ketone (4-tertiary-butyl-3,4-dinitro-2,6 dimethylacetophenone) | 43 |
| Heliotropin (Piperonal) | 19 |
| Phenyl ethyl salicylate | 6 |
| Geraniol | 162 |
| Citronellol | 154 |
| Eugenol, USP | 6 |
| Cinnamic alcohol | 57 |
| Benzyl salicylate | 7 |
| Resin Galbanum | 9 |
| Civet, 2% Tincture | 105 |
| Phenyl ethyl cinnamate | 6 |
| Hexyl cinnamic aldehyde | 12 |
| Iso-Eugenol, extra | 6 |
| Cyclamen aldehyde | 8 |
| Terpineol | 34 |
| Total | 1000 |

EXAMPLE VII

In this example the test is described by which the threshold levels of the 4,4,6-trimethyl-2-cyclohexenone (compound II) and the 2,4,4-trimethyl-2-cyclohexenone (compound IV) were determined.

After a preliminary screening to determine the approximate dilutions required, dilutions of each compound (II and IV) were prepared in increments of three between 0.003% and 0.1% (i.e. 0.1%, 0.03%, 0.01%, 0.003% solutions in diethyl phthalate). These samples were randomly coded by a technician who was not otherwise involved in the evaluation and who was the only person knowing the code.

The samples were evaluated by a five membered panel (one research perfumer, one flavor chemist and three organic chemists). The triangulation method was used for each sample wherein each sample was compared with diethylphthalate controls. The results of the test were written down independently by each member and the data compiled by code number. The technician then provided the code and the data was compiled as follows:

RESULTS

| Compound concentration (wt.%) | Compound[a] II | IV |
|---|---|---|
| 0.10 | 5 | 5 |
| 0.03 | 5 | 1[b] |
| 0.01 | 4 | 1[b] |
| 0.003 | 3 | 0 |

[a]Number of panelists (out of five) able to detect the odor.
[b]The only panelist detecting at this level was the research perfumer.

In summary the lowest range of detection was the following:

Compound II 0.003 – 0.01%
Compound IV 0.03 – 0.1%

This demonstrates that the threshold level of II (4,4,6-trimethyl-2-cyclohexenone) is ten times lower than the threshold level of compound IV (2,4,4-trimethyl-2-cyclohexenone).

The "Manual on Sensory Testing Methods", published by the American Society for Testing and Materials, 1916 Race St., Philadelphia, Pa. 19103 discusses "Threshold Methods" on page 29 and "Triangle Tests" on page 39 and is the basis for the above test method.

We claim:

1. A fragrance composition comprising an olfactorily effective amount of 4,4,6-trimethyl-2-cyclohexenone and at least one other olfactory agent.

2. A composition of claim 1 wherein the olfactory effective amount of 4,4,6-trimethyl-2-cyclohexenone is between 0.1% and 80%.

3. A composition of claim 1 usable as a substitute for a natural oil in fragrances.

4. The composition of claim 3 wherein the natural oil is cedar leaf oil.

5. A method for improving the odor of a fragrance composition which comprises adding thereto a proportion of 4,4,6-trimethyl-2-cyclohexenone.

6. The method of claim 5 wherein the fragrance composition can be used as a substitute for cedar leaf oil.

7. The method of claim 6 wherein the 4,4,6-trimethyl-2-cyclohexenone is added thereto in an amount of about 60 per cent by weight.

8. The method of claim 5 wherein the 4,4,6-trimethyl-2-cyclohexenone is added to the fragrance compositions in an amount sufficient to impart thereto a natural, warm, herbaceous, minty, camphoraceous note.

* * * * *